United States Patent [19]

Masaki et al.

[11] 4,009,168
[45] Feb. 22, 1977

[54] PYRIDINETHIOL-TIN COMPOUND AND PROCESS FOR THE PREPARATION OF THE SAME

[75] Inventors: Mitsuo Masaki; Satoshi Matsunami; Jyunichiro Kita; Toshikazu Hayashi, all of Ichihara, Japan

[73] Assignee: UBE Industries, Ltd., Ube, Japan

[22] Filed: Feb. 7, 1974

[21] Appl. No.: 440,382

[30] Foreign Application Priority Data

Aug. 24, 1973  Japan .............................. 48-94306

[52] U.S. Cl. ..................... 260/270 K; 260/294.8 J; 260/45.75 S
[51] Int. Cl.² ...................................... C07D 213/70
[58] Field of Search ................. 260/270 K, 45.75 S

[56] References Cited

UNITED STATES PATENTS

| | | | |
|---|---|---|---|
| 2,809,971 | 10/1957 | Bernstein | 260/270 K |
| 3,027,372 | 3/1962 | Starrs | 424/245 |
| 3,335,146 | 8/1967 | Reifschneider | 260/270 K |
| 3,346,578 | 10/1967 | Langlykke | 260/270 K |
| 3,533,993 | 10/1970 | Hovey | 260/45.75 S |

OTHER PUBLICATIONS

Petridis et al., Chem. Abs. 73, 30445y (1970).
Kennedy et al., Can J. Chem. 50, 3488 (1972).

*Primary Examiner*—Nicholas S. Rizzo
*Assistant Examiner*—Mark L. Berch
*Attorney, Agent, or Firm*—Flynn & Frishauf

[57] ABSTRACT

Pyridinethiol-tin compounds having the formula of RS-SnX$_2$-SR' in which R and R' are groups derived from unsubstituted or substituted pyridines or unsubstituted or substituted pyridine N-oxides. A process for the preparation of the same is also discosed. The compounds are stabilizers for polyolefins.

19 Claims, No Drawings

PYRIDINETHIOL-TIN COMPOUND AND PROCESS FOR THE PREPARATION OF THE SAME

This invention relates to a novel pyridinethiol-tin compound and a process for the preparation of the same. More particularly, this invention is concerned with a pyridinethiol-tin compound having the general formula RS-SnX$_2$-SR' wherein each of R and R' represents a group which is selected from the class consisting of groups having the general formulae

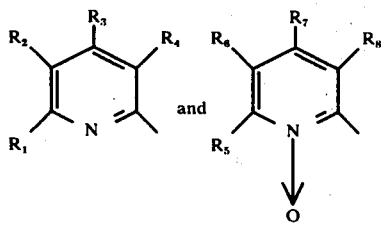

wherein each of R$_1$ – R$_8$ represents a group which is selected from the class consisting of hydrogen atom, a halogen atom, nitro group, nitroso group, an amino group, cyano group, carboxyl group, a carbamoyl group, a thiocarbamoyl group, an alkoxycarbonyl group having carbon atoms of 2–11, hydroxyl group, a hydrazinocarbonyl group, mercapto group, acyloxy, alkoxy and acylamino groups each having carbon atoms of 1–10, and a group selected from the class consisting of phenyl group and the substituted group thereof, linear and branched alkyl groups each having carbon atoms of 1–12 and the substituted groups thereof, linear and branched alkenyl groups each having atoms of 2–12 and the substituted groups thereof and aralkyl and alkallyl groups each having carbon atoms of 7–12 and the substituted groups thereof wherein the substituents in the substituted groups are groups selected from the class consisting of a halogen atom and the above-mentioned groups, and not less than two groups among each of R$_1$ – R$_4$ and R$_5$ – R$_8$ represent groups selected from the class consisting of hydrogen atom and unsubstituted linear and branched alkyl groups each having carbon atoms of 1–12 and there is no case where all of R$_5$, R$_6$, R$_7$ and R$_8$ are hydrogen atoms, and X represents an atom which is selected from the class consisting of fluorine, chlorine, bromine and iodine, and a process for the preparation of the same.

The object of this invention is to provide a novel pyridinethiol-tin compound which can act as an excellent stabilizer for polyolefins. A further object is to provide the pyridinethiol-tin compound which can produce an excellent stabilizing effect against deteriorations caused by contact with heavy metals on polyolefins. Another object is to provide a process for the preparation of the pyridinethiol-tin compound by reacting 2,2'-dipyridyl disulfide having the formula RS-SR' with a stannous halide having the formula SnX$_2$. Other objects of this invention will be obvious from the contents of the specification hereinafter disclosed.

R and R' of the above-mentioned 2,2'-dipyridyl disulfide are concretely exemplified by 2-pyridyl groups, 3-nitro-2-pyridyl groups, 5-nitro-2-pyridyl groups, 3-nitro-5-methyl-2-pyridyl groups, 3-chloro-5-nitro-2-pyridyl groups, 3-bromo-5-nitro-2-pyridyl groups, 3-iodo-5-nitro-2-pyridyl groups, 3-nitro-5-acetamido-2-pyridyl groups, 3-nitro-5-amino-2-pyridyl groups, 5-cyano-2-pyridyl groups, 3-cyano-6-undecanyl-2-pyridyl groups, 3-cyano-4,6-dimethyl-2-pyridyl groups, 3-cyano-4-ethoxycarbonyl-6-methyl-2-pyridyl groups, 3-cyano-4-methyl-6-phenyl-2-pyridyl groups, 3-cyano-4,6-dimethyl-5-acetyloxy-2-pyridyl groups, 3-cyano-6-methyl-2-pyridyl groups, 3-cyano-4,6-dimethyl-5-amino-2-pyridyl groups, 5-acetamido-2-pyridyl groups, 3-acetamido-6-chloro-2-pyridyl groups, 3-amino-6-methoxy-2-pyridyl groups, 3-amino-6-ethoxy-2-pyridyl groups, 5-amino-2-pyridyl groups, 3-amino-6-chloro-2-pyridyl groups, 3-amino-2-pyridyl groups, 3-hydrazinocarbonyl-2-pyridyl groups, 5-carbamoyl-2-pyridyl groups, 5-thiocarbamoyl-2-pyridyl groups, 3-chloro-5-thiocarbamoyl-2-pyridyl groups, 3-bromo-5-thiocarbamoyl-2-pyridyl groups, 3-iodo-5-thiocarbamoyl-2-pyridyl groups, 3-methoxycarbonyl-2-pyridyl groups, 4-methoxycarbonyl-6-mercapto-2-pyridyl groups, 3-ethoxycarbonyl-6-methyl-2-pyridyl groups, 3-carboxy-4-mercapto-2-pyridyl groups, 3-carboxy-2-pyridyl groups, 3-chloro-5-carboxy-2-pyridyl groups, 3-bromo-5-carboxy-2-pyridyl groups, 3-iodo-5-carboxy-2-pyridyl groups, 3-carboxy-4,6-dimethyl-2-pyridyl groups, 5-chloro-2-pyridyl groups, 5-bromo-2-pyridyl groups, 5-iodo-2-pyridyl groups, 3,5-dibromo-2-pyridyl groups, 3,5-diiodo-2-pyridyl groups, 3-methyl-2-pyridyl groups, 4-methyl-2-pyridyl groups, 5-methyl-2-pyridyl groups, 6-methyl-2-pyridyl groups, 3-ethyl-6-methyl-2-pyridyl groups, 4,6-dimethyl-2-pyridyl groups, 5,6-dimethyl-2-pyridyl groups, 4,6-diethyl-2-pyridyl groups, 4-ethyl-5,6-dimethyl-2-pyridyl groups, 5-ethyl-4,6-dimethyl-2-pyridyl groups, 4-ethyl-3,5,6-trimethyl-2-pyridyl groups, 3-phenyl-2-pyridyl groups, 4-methyl-6-phenyl-2-pyridyl groups, 4-methyl-6-para-tolyl-2-pyridyl groups, 4,6-diphenyl-2-pyridyl groups, N-oxido-5-bromo-2-pyridyl groups, N-oxido-6-chloro-2-pyridyl groups, N-oxido-4-nitro-2-pyridyl groups, N-oxido-3-methyl-2-pyridyl groups, N-oxido-6-methyl-2-pyridyl groups, N-oxido-4-propyl-2-pyridyl groups, N-oxido-3-ethyl-6-methyl-2-pyridyl groups, N-oxido-4,6-dimethyl-2-pyridyl groups, N-oxido-4,5-dimethyl-2-pyridyl groups, N-oxido-4-methyl-2-pyridyl groups, N-oxido-3,4-dimethyl-2-pyridyl groups and N-oxido-5-methyl-2-pyridyl groups.

Dipyridyl disulfides are concretely exemplified by 2,2'-dipyridyl disulfide, bis(5-chloro-2-pyridyl) disulfide, bis(5-bromo-2-pyridyl) disulfide, bis(5-iodo-2-pyridyl) disulfide, bis(3-nitro-2-pyridyl) disulfide, bis(5-nitro-2-pyridyl) disulfide, bis(3-nitro-5-methyl-2-pyridyl) disulfide, bis(3-chloro-5-nitro-2-pyridyl) disulfide, bis(5-acetamido-2-pyridyl) disulfide, bis(3-amino-6-chloro-2-pyridyl) disulfide, bis(3-cyano-6-methyl-2-pyridyl) disulfide, bis(3-acetamido-6-chloro-2-pyridyl) disulfide, bis(3-cyano-4,6-dimethyl-2-pyridyl) disulfide, bis(3-cyano-4-methyl-6-phenyl-2-pyridyl) disulfide, bis(3-methyl-2-pyridyl) disulfide, bis(4-methyl-2-pyridyl) disulfide, bis(5-methyl-2-pyridyl) disulfide, bis(6-methyl-2-pyridyl) disulfide, bis(3-phenyl-2-pyridyl) disulfide, bis(4,6-dimethyl-2-pyridyl) disulfide, bis(5,6-dimethyl-2-pyridyl) disulfide, bis(3-ethyl-6-methyl-2-pyridyl) disulfide, bis(4,6-diethyl-2-pyridyl) disulfide, bis(4-methyl-6-phenyl-2-pyridyl) disulfide, bis(4,6-diphenyl-2-pyridyl) disulfide, bis(4-methyl-6-para-tolyl-2-pyridyl) disulfide, bis(4-ethyl-5,6-dimethyl-2-pyridyl) disulfide, bis(4,6-dimethyl-5-ethyl-2-pyridyl) disulfide, bis(3,5,6-trimethyl-4-ethyl-2-pyridyl) disulfide, (6-methyl-2-pyridyl) (2'-pyridyl) disulfide, (4,6-dimethyl-2-pyridyl) (2'-pyridyl) disulfide, (4-methyl-6-phenyl-2-pyridyl) (2'-pyridyl) disulfide, bis(3-ethoxycarbonyl-6-methyl-2-pyridyl) disulfide, (N-oxido-4,6-dimethyl-2-pyridyl) (2'-pyridyl) disulfide, (N-oxido-6-chloro-2-pyridyl) (4', 6'-dimethyl-2'-pyridyl) disulfide, bis(N-oxido-6-chloro-2-pyridyl) disulfide, bis(N-oxido-- 5-bromo-2-pyridyl) disulfide, bis(N-oxido-4-nitro-2-pyridyl) disulfide, bis(N-oxido-- 3-ethyl-6-methyl-2-pyridyl) disulfide, bis(N-oxido-4,6-dimethyl-2-pyridyl) disulfide, bis(N-oxido-4,5-dimethyl-2-pyridyl) disulfide, bis(N-oxido-4-methyl-2-pyridyl) disulfide, bis(N-oxido-3-methyl-2-pyridyl) disulfide, bis(N-oxido-4-propyl-2-pyridyl) disulfide, bis (N-oxido-6-methyl-2-pyridyl) disulfide, bis-(IV-oxido-3,4-dimethyl-2-pyridyl) disulfide and bis (N-oxido-5-methyl-2-pyridyl) disulfide.

Stannous halides are exemplified by stannous chloride, stannous bromide, stannous iodide and stannous fluoride, and may be in anhydrous state or in hydrated state.

The pyridinethiol-tin compounds having the aforementioned general formula $RS-SnX_2-SR'$ may be synthesized by reacting the aforementioned dipyridyl disulfide with stannous halide in the presence or absence of an organic solvent. The organic solvent employed in the reaction may be exemplified by an aliphatic or alicyclic hydrocarbon such as, for instance, pentane, hexane, heptane, ligroin or cyclohexane, an aromatic hydrocarbon or its halogenated derivative such as, for instance, benzene, toluene, xylene or chlorobenzene, a halogenated hydrocarbon such as, for instance, chloroform, methylene chloride, carbon tetrachloride or ethylene dichloride, an alcohol such as, for instance, methanol, ethanol, propanol, cyclohexanol, ethylene glycol or diethylene glycol, and ketone such as, for instance, acetone, methyl ethyl ketone or methyl isobutyl ketone. Of these organic solvents those in which the aforementioned disulfide is soluble are preferred.

If a substance which can react with stannous halide to give a complex compound soluble in the aforementioned organic solvent, such as an organic Lewis base, for example, dioxane, tetrahydrofuran, diethyl ether, dipropyl ether, dibutyl ether, diethylene glycol dimethyl ether, N,N-dimethylformamide, caprolactam, dimethyl sulfoxide or triphenylphosphine oxide is used as an additive in the aforementioned reaction, the reaction may be promoted and separation of a solid reaction product from unreacted stannous halide becomes easy. The amount of the organic Lewis base to be added may be between a small amount such as 0.01 mole to 1 mole of stannous halide and such a large amount that said base itself may serve as a solvent. In case where the organic Lewis base is employed in a small amount, said base forms a complex compound with a part of the stannous halide. The stannous halide reacts in the form of complex, and then an organic Lewis base liberated by the reaction again forms a complex compound with an another part of the stannous halide.

The reaction is preferably conducted using equimolecular quantities of the starting compounds. Yet, a slight excess of the amount of either compound may also be employed.

The reaction temperature and time to be employed may vary upon, for example, the kind of the aforementioned dipyridyl disulfide and/or the kind and/or a reacting amount of stannous halide. The reaction temperature is set below the decomposition temperature of the above dipyridyl disulfide and may generally be between 0° and 150° C. The reaction may be carried out in the absence of an organic solvent and at a temperature ranging from the melting point of the dipyridyl disulfide to be used to the decomposition point thereof. The reaction time may generally be between 10 minutes and 12 hours.

The separation of the pyridinethiol-tin compound having the general formula $RS-SnX_2-SR'$, a reaction product, from the reaction mixture may be carried out by filtration of the reaction mixture and subsequent washing and/or recrystallization of the collected crude product using cooled water or an organic solvent such as, methylene chloride, ethylene dichloride, carbon tetrachloride, acetonitrile, benzene, xylene, toluene, etc. or alternative extraction of the collected crude product with, for example, hot benzene, hot toluene or hot acetonitrile.

The aforementioned pyridinethiol-tin compounds may concretely be exemplified by dichloro bis(2-pyridylthio)tin(IV), dibromo bis(2-pyridylthio)tin(IV), diiodo bis(2-pyridylthio)tin(IV), difluoro bis(2-pyridylthio)tin(IV), dichloro bis(3-nitro-2-pyridylthio)tin(IV), dichloro bis(5-nitro-2-pyridylthio)tin(IV), dichloro bis(5-acetamido-2-pyridylthio)tin(IV), dichloro bis(3-acetamido-6-chloro-2-pyridylthio)tin(IV), dichloro bis(3-ethoxycarbonyl-6-methyl-2-pyridylthio)tin(IV), dichloro bis(5-chloro-2-pyridylthio)tin(IV), dichloro bis(5-bromo-2-pyridylthio)tin(IV), dichloro bis(5-iodo-2-pyridylthio)tin(IV), dichloro bis(3-chloro-5-nitro-2-pyridylthio)tin(IV), dichloro bis(3-cyano-4,6-dimethyl-2-pyridylthio)tin(IV), dibromo bis(3-cyano-4,6-dimethyl-2-pyridylthio)tin(IV), diiodo bis(3-cyano-4,6-dimethyl-2-pyridylthio)tin(IV), difluoro bis(3-cyano-4,6-dimethyl-2-pyridylthio)tin(IV), dichloro bis(3-cyano-4-methyl-6-phenyl-2-pyridylthio)tin(IV), dibromo bis(3-cyano-4-methyl-6-phenyl-2-pyridylthio)tin(IV), diiodo bis(3-cyano-4-methyl-6-phenyl-2-pyridylthio)tin(IV), difluoro bis(3-cyano-4-methyl-6-phenyl-2-pyridylthio)tin(IV), dichloro bis(3-cyano-6-methyl-2-pyridylthio)tin(IV), dibromo bis(3-cyano-6-methyl-2-pyridylthio)tin(IV), diiodo bis(3-cyano-6-methyl-2-pyridylthio)tin(IV), difluoro bis(3-cyano-6-methyl-2-pyridylthio)tin(IV), dichloro bis(5-methyl-3-nitro-2-pyridylthio)tin(IV), dichloro bis(4,6-dimethyl-2-pyridylthio)tin(IV), dibromo bis(4,6-dimethyl-2-pyridylthio)tin(IV), diido bis(4,6-dimethyl-2-pyridylthio)tin(IV), difluoro bis(4,6-dimethyl-2-pyridylthio)tin(IV), dichloro bis(4,6-diethyl-2-pyridylthio)tin(IV), dibromo bis(4,6-diethyl-2-pyridylthio)tin(IV), dichloro bis(4-methyl-6-phenyl-2-pyridylthio)tin(IV), dibromo bis(4-methyl-6-phenyl-2-pyridylthio)tin(IV), diiodo bis(4-methyl-6-phenyl-2-pyridylthio)tin(IV), difluoro bis(4-methyl-6-phenyl-2-pyridylthio)tin(IV), dichloro bis(3-amino-6-chloro-2-pyridylthio)tin(IV), dichloro bis(3-methyl-2-pyridylthio)tin(IV), dichloro bis(4-methyl-2-pyridylthio)tin(IV), dichloro bis(5-methyl-2-pyridylthio)tin(IV), dichloro bis(6-methyl-2-pyridylthio)tin(IV), dibromo bis(6-methyl-2-pyridylthio)tin(IV), diiodo bis(6-methyl-2-pyridylthio)tin(IV), difluoro bis(6-methyl-2-pyridylthio)tin(IV), dichloro bis(3-phenyl-2-pyridylthio)tin(IV), dichloro bis(5,6-dimethyl-2-pyridylthio)tin(IV), dichloro bis(3-ethyl-6-methyl-2-pyridylthio)tin(IV), dichloro bis(4,6-diphenyl-2-pyridylthio)tin(IV), dichloro bis(4-methyl-6-para-tolyl-2-pyridylthio)tin(IV), dichloro bis(4-ethyl-5,6-dimethyl-2-pyridylthio)tin(IV), dichloro bis(5-ethyl-4,6-dimethyl-2-pyridylthio)tin(IV), dichloro bis(3,5,6- trimethyl-4-ethyl-2-pyridylthio)tin(IV), dichloro (4,6-dimethyl-2-pyridylthio) (2'-pyridylthio)tin(IV), dichloro (4-methyl-6-phenyl-2-pyridylthio) (2'-pyridylthio)tin(IV), dichloro (6-methyl-2-pyridylthio) (2'-pyridylthio)tin(IV), dichloro bis(N-oxido-- 4-nitro-2-pyridylthio)tin(IV), dichloro bis(N-oxido-6-chloro-2-pyridylthio)tin(IV), dichloro bis(N-oxido-3-ethyl-6-methyl-2-pyridylthio)tin(IV), dichloro (N-oxido-4,6-dimethyl-2-pyridylthio) (2'-pyridylthio)tin(IV), dichloro (N-oxido-6-chloro-2-pyridylthio) (4',6'-dimethyl-2'pyridylthio)tin(IV), dichloro bis(N-oxido-5-bromo-2-pyridylthio)tin(IV), dichloro bis(N-oxido-4-propyl-2-pyridylthio)tin(IV), dichloro bis(N-oxido-4,6-dimethyl-2-pyridylthio)tin(IV), dichloro bis(N-oxido-4,5-dimethyl-2-pyridylthio)tin(IV), dichloro bis(N-oxido-4-methyl-2-pyridylthio)tin(IV), dichloro bis(N-oxido-3,4-dimethyl-2-pyridylthio)tin(IV), dichloro bis(N-oxido-5-methyl-2-pyridylthio)tin(IV), dichloro bis(N-oxido-3-methyl-2-pyridylthio)tin(IV) and dichloro bis(N-oxido-6-methyl-2-pyridylthio)tin-(IV).

The pyridinethiol-tin compounds obtained according to this invention show an extremely excellent effect as a stabilizer for polyolefins especially against their deteriorations caused by contact with heavy metals.

This invention will be illustrated in the following examples.

EXAMPLE 1

Synthesis of dichloro bis(2-pyridylthio)tin(IV)

To 150 ml of benzene were added 33.95 g of $\epsilon$-caprolactam and 28.44 g of stannous chloride. They were mixed to dissolve. To the solution was added dropwise with stirring at room temperature a solution of 33.05 g of 2,2'-dipyridyl disulfide in 150 ml of benzene. With addition, pale yellow crystals precipitated. After completion of the addition, the resultant mixture was stirred at room temperature for 3 hours and filtered. Crystals collected by the filtration were suspended in 350 ml of ethylene dichloride. After stirring, the suspended crystals were collected by filtration. The collected crystals were washed with 50 ml of ethylene dichloride and then with 100 ml of benzene and dried to give 57.27 g of almost colorless cyrstals with slight yellowness, melting at 275° – 277° C.

The elemental analytical results of these crystals are shown below.

Found: C, 29.32%; H, 1.92%; N, 6.78%; S, 15.90%; Cl, 17.56%. Calcd. for $C_{10}H_8N_2S_2SnCl_2$: C, 29.30%; H, 1.97%; N, 6.83%; S, 15.64%; Cl, 17.30%.

The obtained crystals showed a parent peak at 410 in Mass Spectra. This result exhibits that said crystals have molecular weight of 410 and, therefore, the obtained crystals evidently has a molecular formula of $C_{10}H_8N_2S_2SnCl_2$, on the basis of the above elemental anayltical results.

In order to confirm that the obtained crystals should be identified as dichloro bis(2-pyridylthio)tin(IV), the following experiments were carried out.

Dichloro bis(2-pyridylthio)tin(IV) was synthesized from several kinds of tetracovalent chlorotin compounds according to three other methods shown below.

a. Dichloro bis(acetylacetonato)tin(IV), which was a known compound, and double molar quantity of 2-pyridinethiol were caused to react in an organic solvent at room temperature to give dichloro bis(2-pyridylthio)tin(IV) in a yield of 93.7 % as well as acetylacetone. (Refer to Referential example 1)

b. 2-Pyridinethiol and 0.5 times molar quantity of stannic chloride were caused to react in water to give dichloro bis(2-pyridylthio)tin(IV) in a yield of 90.4 %. (Refer to Referential example 2)

c. 2-Pyridinethiol-stannic chloride complex (2:1 in molar ratio) which was prepared by reaction of 2-pyridinethiol and 0.5 times molar quantity of stannic chloride in an organic solvent under nonaqueous condition (Refer to Referential example 3) was caused to react with triethylenediamine being a strong organic base in an organic solvent to give dichloro bis(2-pyridylthio)tin(IV) in a yield of 98.0 % as well as hydrochloride of the employed base. (Refer to Referential example 4)

The dichloro bis(2-pyridylthio)tin(IV) obtained by these methods precisely agreed with the aforementioned crystals in their melting points and IR spectra. Accordingly, the aforementioned crystals are evidently identified as a compound having tetracovalent tin atom.

In addition, the aforementioned crystals showed, in Mass Spectra, peaks at 300, 265 and 230 which were assigned to fragments of

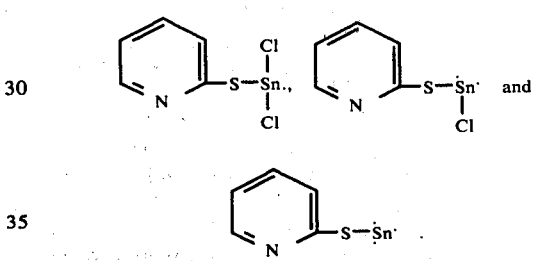

These results apparently evidence that the aforementioned crystals have the following formula which would prove an insertion of stannous chloride in between the S-S bond of 2,2'-dipyridyl disulfide and oxidation of the tin atom into tetracovalent.

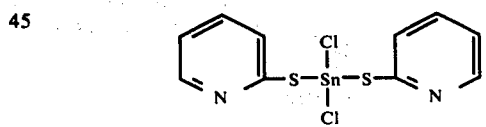

Further, treatment of the above crystals with imidazole which should have stronger coordination ability to a tin atom than 2,2'-dipyridyl disulfide did not make any change of said crystals, and the employed imidazole as such was recovered. (Refer to Referential example 5) If the crystals were assumed to be a complex compound with a divalent tin atom wherein 2,2'-dipyridyl disulfide merely coordinates to stannous chloride, the above-mentioned treatment causes a transfer of stannous chloride from 2,2'-dipyridyl disulfide to imidazole having stronger coordination ability (ligand exchange reaction) and therefore gives a stannous chloride complex compound of imidazole and make 2,2'-dipyridyl disulfide free.

The fact that in coordination ability to tin atom imidazole is stronger than 2,2'-dipyridyl disulfide is proved by the experiment in which 2,2'-dipyridyl disulfide-stannic chloride complex (1:1 in molar ratio) was treated with imidazole to give 2,2'-dipyridyl disulfide and imidazole-stannic chloride complex (2:1 in molar ratio). (Refer to Referential examples 6 and 7) Therefore, it is also confirmed that the aforementioned crystals have the above-identified formula containing tetracovalent tin atom by the fact that the treated crystals were recovered unchanged without letting 2,2'-dipyridyl disulfide free in the reaction with imidazole.

In addition, since a tetracovalent tin atom can have a coordination number of 6, dichloro bis(2-pyridylthio)tin(IV) may have, under certain conditions, the resonance structures shown below. In this invention, said structures are typified by the aforementioned limit-structural formula.

To a solution of 2.67 g of 2-pyridinethiol in 80 ml of ethylene dichloride was added dropwise with stirring at room temperature 20 ml of ethylene dichloride containing 3.13 g of stannic chloride. With addition, yellow crystals began to precipitate. After the addition was completed, when a temperature of the reaction mixture rose by 5° C, stirring was continued for another 4 hours and the reaction mixture was filtered. The collected crystals were washed with 30 ml of ethylene dichloride and dried to give 5.79 g of yellow crystals. Those crystals had a melting point of 224°~226° C and were identified as 2-pyridinethiol-stannic chloride complex (2:1 in molar ratio) by IR spectrum and the elemental analyses.

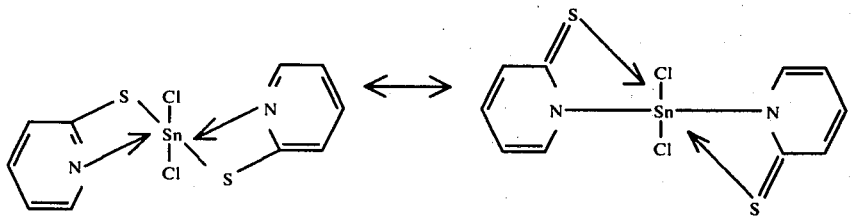

REFERENTIAL EXAMPLE 1

Synthesis of dichloro bis(2-pyridylthio)tin(IV) by the reaction of dichloro bis(acetylacetonato)tin(IV) with 2-pyridinethiol in a benzene solution.

To a solution of 3.88 g of dichloro bis-(acetylacetonato)tin(IV) in 100 ml of benzene was added 2.22 g of 2-pyridinethiol and the mixture was stirred at room temperature. With dissolution of crystals of 2-pyridinethiol, other crystals freshly began to precipitate. The mixture was stirred overnight at room temperature and filtered. The collected residue was washed with 50 ml of benzene and dried to give 3.84 g of dichloro bis(2-pyridylthio)tin(IV) as almost colorless crystals with slight yellowness. The obtained crystals had a melting point of 275°~277° C. IR spectrum thereof was superimposable on that of the crystals obtained in Example 1.

In addition, it was ascertained by gas chromatography that the benzene filtrate separated from the crystals contained acetylacetone.

REFERENTIAL EXAMPLE 2

Synthesis of dichloro bis(2-pyridylthio)tin(IV) by the reaction of 2-pyridinethiol with stannic chloride in an aqueous solution.

To a solution of 4.44 g of 2-pyridinethiol in 50 ml of water was added dropwise with stirring at room temperature 30 ml of an aqueous solution containing 7.7 g of stannic chloride pentahydrate. With addition, crystals precipitated. After completion of the addition, stirring was continued overnight at room temperature, and the reaction mixture was filtered. The collected crystals were washed with 30 ml of cooled water and dried to give 7.40 g of dichloro bis(2-pyridylthio)tin-(IV) as almost colorless crystals with slight yellowness. The obtained crystals had a melting point of 275°~277° C. IR spectrum thereof was superimposable on that of the crystals obtained in Example 1.

REFERENTIAL EXAMPLE 3

Synthesis of 2-pyridinethiol-stannic chloride complex

Found: C, 25.22%; H, 2.12%; N, 6.11%; S, 13.34%; Cl, 29.10%. Calcd. for $C_{10}H_{10}N_2S_2SnCl_4$: C, 24.87%; H, 2.09%; N, 5.80%; S, 13.28%; Cl, 29.37%.

REFERENTIAL EXAMPLE 4

Synthesis of dichloro bis(2-pyridylthio)tin(IV) by the reaction of 2-pyridinethiol-stannic chloride complex with triethylenediamine To 120 ml of benzene was added 12.07 g of 2-pyridinethiol-stannic chloride complex (2:1 in molar ratio) and the mixture was stirred. To the suspension was added dropwise at room temperature a solution of 2.81 g of triethylenediamine in 30 ml of benzene. A slightly exothermic reaction occurred upon the addition, and a temperature of the reaction mixture rose by 6° C when the addition was completed. After the completion of the addition, the mixture was stirred at room temperature for 18 minutes and then refluxed by heating for 2 hours. After termination of the heating, stirring was continued for another 2 hours. The reaction mixture was filtered to give 14.69 g of crystals. The crystals were identified as a mixture of those of dichloro bis(2-pyridylthio)tin(IV) and those of triethylenediamine dihydrochloride by the IR spectrum.

These crystals were then added to 50 ml of ice-water. By stirring for ten minutes, the triethylenediamine dihydrochloride was dissolved. After filtration of this aqueous mixture, collected crystals were washed with three 10 ml portions of cooled water and dried to give 10.04 g of almost colorless crystals with slight yellowness. The obtained crystals had a melting point of 274°~276° C. IR spectrum thereof was superimposable on that of the crystals obtained in Example 1.

REFERENTIAL EXAMPLE 5

Influence of imidazole on dichloro bis(2-pyridylthio)tin(IV)

To a solution of 1.36 g of imidazole in 60 ml of isopropanol was added 4.10 g of dichloro bis(2-pyridylthio)tin(IV). The mixture was stirred at room temperature for 5 hours and then filtered. The collected residue was washed with 50 ml of isopropanol and dried to give 3.85 g of crystals. The obtained crystals had a melting point of 275°~276° C. IR spectrum thereof was superimposable on that of dichloro bis(2-pyridylthio)tin(IV) firstly used in this Referential example. The combined filtrate and washings were concentrated under reduced pressure, whereby imidazole was quantitatively recovered.

REFERENTIAL EXAMPLE 6

Synthesis of 2,2'-dipyridyl disulfide-stannic chloride complex

To a solution of 2.20 g of 2,2'-dipyridyl disulfide in 30 ml of benzene was added dropwise at room temperature a solution of 2.61 g of stannic chloride in 20 ml of benzene. A slightly exothermic reaction occurred upon the addition and a temperature of the reaction mixture rose by 6° C. After completion of the addition, stirring was continued at room temperature for 5 hours. The reaction mixture was filtered, and the collected substance was dried to give 4.38 g of yellow crystals. The crystals had a melting point of 98° – 101° c and were identified as 2,2'-dipyridyl disulfide-stannic chloride complex (1:1 in molar ratio) by IR spectrum and the elemental analyses.

Found: C, 25.53%; H, 1.91%; N, 5.73%; S, 13.05%; Cl, 29.335%. Calcd. for $C_{10}H_8N_2S_2SnCl_4$: C, 24.98%; H, 1.68%; N, 5.83%; S, 13.34%; Cl, 29.50%.

REFERENTIAL EXAMPLE 7

Reaction of 2,2'-dipyridyl disulfide-stannic chloride complex with imidazole

To 100 ml of ethylene dichloride were added 4.81 g of 2,2'-dipyridyl disulfide-stannic chloride complex and then 1.36 g of imidazole, and the mixture was stirred at room temperature. Crystals of imidazole dissolved and other crystals newly precipitated. After stirring for 5 hours, the reaction mixture was filtered and the collected crystals were dried to give 3.96 g of colorless crystals. In determination of a melting point, the crystals began to sinter with coloration of black at 286° C and completely decomposed at 322° C. The obtained substance was identified by IR spectrum as imidazole-stannic chloride complex (2:1 in molar ratio) which was synthesized separately from 2 moles of imidazole and 1 mole of stannic chloride.

In addition, the filtrate obtained by the filtration leaving 3.96 g of the above-mentioned colorless crystals was concentrated and ethylene dichloride was recovered. The residue was washed with 60 ml of water to give 2.16 g of 2,2'-dipyridyl disulfide as water-insoluble crystals. The relative recovery of the disulfide was 98.2 % based on 2,2'-dipyridyl disulfide-stannic chloride complex employed.

EXAMPLE 2

Synthesis of dibromo bis(2-pyridylthio)tin(IV)

To 50 ml of ethylene dichloride was added 5.38 g of stannous bromide monohydrate. To the stirred mixture was added dropwise at room temperature a solution of 4.00 g of 2,2'-dipyridyl disulfide in 50 ml of ethylene dichloride. A slightly exothermic reaction occurred and a temperature of the reaction mixture rose by 2° –3° C. The crystals of stannous bromide monohydrate gradually dissolved and yellow crystals became to precipitate. After completion of the addition, stirring was continued at room temperature for 5 hours. The reaction mixture was filtered and the collected crystals were dried to give 7.32 g of yellow crystals. The obtained crystals had a melting point of 278° –280° C and were identified by IR spectrum and the elemental analyses as dibromo bis(2-pyridylthio)tin(IV).

Found: C, 24.30%; H, 1.66%; N, 5.62%; S, 12.78%. Calcd. for $C_{10}H_8N_2S_2SnBr_2$:C, 24.08%; H, 1.62%; N, 5.62%; S, 12.85%.

EXAMPLE 3

Synthesis of dichloro bis(3-cyano-4,6-dimethyl-2-pyridylthio)tin(IV)

To a solution of 2.39 g of ε-caprolactam and 2.84 g of stannous chloride in 40 ml of benzene was added dropwise with stirring at room temperature a solution of 4.90 g of bis(3-cyano-4,6-dimethyl-2-pyridyl) disulfide in 90 ml of benzene. There was no noticeable change of the temperature of the mixture during the addition and the reaction mixture remained in homogeneous state. After a few minutes upon completion of addition, pale-yellow crystals began to precipitate. The resultant mixture was stirred for 1 hour after the completion of the addition, and the reaction mixture was filtered. The collected substance was dried to give 5.71 g of pale-yellow crystals. The crystals were recrystallized from ethylene dichloride. mp 159° – 260° C (decomp.) The recrystallized crystals were identified by the elemental analyses and IR spectrum as dichloro bis(3-cyano-4,6-dimethyl-2-pyridylthio)tin(IV).

Found: C, 37.29%; H, 2.72%; N, 10.87%; S, 12.29%; Cl, 14.15%. Calcd. for $C_{16}H_{14}N_4S_2SnCl_2$: C, 37.24%; H, 2.73%; N, 10.86%; S, 12.43%; Cl, 13.74%.

The solution obtained by filtration leaving the above-mentioned crystals was concentrated, whereby benzene was recovered. The residue was washed with 40 ml of carbon tetrachloride and then 30 ml of ethylene dichloride and dried to give 1.23 g of pale-yellow crystals. It was confirmed by the IR spectrum and a melting point determination that the obtained crystals should be identified as dichloro bis(3-cyano-4,6-dimethyl-2-pyridylthio)tin(IV).

EXAMPLE 4

Synthesis of dichloro bis(3-cyano-4-methyl-6-phenyl-2-pyridylthio)tin(IV).

To a suspension of 100 ml of benzene containing 2.78 g of bis(3-cyano-4-methyl-6-phenyl-2-pyridyl) disulfide (a synthetic method thereof is referred to Referential example 8) was added dropwise with stirring at room temperature a solution of 1.40 g of ε-caprolactam and 1.17 g of stannous chloride in 30 ml of benzene. A slightly exothermic reaction occurred and a temperature of the reaction mixture rose by 1°~2° C. The reaction mixture was gradually becoming orange-yellow and, with gradual dissolution of the crystals of the above-mentioned disulfide, there began to precipitate new crystals. After stirring the mixture overnight at room temperature, the reaction mixture was filtered. The collected substance was dried to give 3.46 g of yellowish crystals. The obtained crystals were recrystallized from benzene. In determination of a melting point, the crystals decomposed at 304°~305° C. The crystals were identified by the elemental analyses and IR spectrum as dichloro bis(3-cyano-4-methyl-6-phenyl-2-pyridylthio)tin(IV).

Found: C, 49.40%; H, 2.93%; N, 8.72%; S, 10.12%; Cl, 10.87%. Calcd. for $C_{26}H_{18}N_4S_2SnCl_2$: C, 48.79%; H, 2.83%; N, 8.75%; S, 10.02%; Cl, 11.08%.

REFERENTIAL EXAMPLE 8

Synthesis of bis(3-cyano-4-methyl-6-phenyl-2-pyridyl) disulfide

An ethanolic solution containing sodium ethoxide was prepared by dissolving 0.74 g of metallic sodium in 70 ml of ethanol. To the solution was added 7.28 g of 3-cyano-4-methyl-6-phenyl-2-pyridinethiol. The mixture was stirred at room temperature for about 20 minutes to give a yellowish homogeneous solution. To this solution was added dropwise with stirring at room temperature 60 ml of ethanol containing 4.09 g of iodine. With addition, colorless crystals began to precipitate and there was obtained a suspension at the time of completion of the addition. After completion of the addition, stirring was continued for about 2 hours at room temperature. The reaction mixture was then filtered and the collected substance was dried to give 7.00 g of brownish crystals. The obtained crystals were recrystallized from benzene. The crystals recrystallized had a melting point of 200°~201° C and were identified by the elemental analyses and IR spectrum as bis(3-cyano-4-methyl-6-phenyl-2-pyridyl) disulfide.

Found: C, 69.46%; H, 3.70%; N, 12.65%; S, 14.16%. Calcd. for $C_{26}H_{18}N_4S_2$: C, 69.31%; H, 4.02%; N, 12.43%; S, 14.23%.

EXAMPLE 5

Synthesis of dichloro bis(N-oxido-2-pyridylthio)tin(IV)

To a suspension of 80 ml of ethylene dichloride containing 4.00 g of bis(N-oxido-2-pyridyl) disulfide was added dropwise with stirring at room temperature a solution of 3.59 g of ε-caprolactam and 3.01 g of stannous chloride in 50 ml of ethylene dichorlide. A slightly exothermic reaction occurred and a temperature of the reaction mixture rose by 3° C. With addition, said disulfide gradually dissolved and there began to precipitate newly colorless crystals. After completion of the addition, the resultant mixture was refluxed by heating with stirring for 45 minutes. After spontaneous cooling, the reaction mixture was filtered. The collected crystals were washed with 20 ml of ethylene dichloride and dried to give 6.52 g of colorless crystals. The obtained crystals had a melting point of 300.5°~302° C (decomp.) and were identified by IR spectrum and the elemental analyses as dichloro bis(N-oxido-2-pyridylthio)tin(IV).

Found: C, 27.13%; H, 1.78%; N, 6.25%; S, 14.10%; Cl, 16.33%. Calcd. for $C_{10}H_8N_2O_2S_2SnCl_2$: C, 27.18%; H, 1.82%; N, 6.34%; S, 14.51%; Cl, 16.05%.

Since both the filtrate obtained by filtration leaving 6.52 g of above colorless crystals and the washing solution contained ε-caprolactam and a small quantity of dichloro bis(N-oxido-2-pyridylthio)tin(IV), these solutions were used for a repeated reaction. 3.01 g of stannous chloride was added to a solution made by combining said filtrate and washings and the mixture was stirred at room temperature. To the resultant clear solution was added 4.00 g of bis(N-oxido-2-pyridyl) disulfide and the mixture was refluxed by heating with stirring for 1 hour. After spontaneous cooling, the reaction mixture was filtered. The collected substance was washed with 20 ml of ethylene dichloride and dried to give 6.95 g of colorless crystals. The obtained crystals had a melting point of 300.5°~302° C (decomp.) IR spectrum of the crystals was superimposable on that of the crystals obtained, in a yield of 6.52 g, by the reaction above identified. From these results, the obtained crystals were also identified as dichloro bis(N-oxido-2-pyridylthio)tin(IV).

EXAMPLE 6

Synthesis of dichloro bis(4,6-dimethyl-2-pyridylthio)tin(IV)

To 50 ml of a benzene solution containing 5.00 g of bis(4,6-dimethyl-2-pyridyl) disulfide (a synthetic method thereof is referred to Referential examples 9 and 10) was added dropwise with stirring a solution of 4.09 g of ε-caprolactam and 3.43 g of stannous chloride in 55 ml of benzene. A slightly exothermic reaction occurred upon addition and a temperature of the reaction mixture rose by 5°~6° C. The reaction mixture remained as a homogeneous solution. After stirring for about 30 minutes from the completion of the addition, there began to precipitate crystals. Stirring was continued overnight and the reaction mixture was filtered. The collected crystals were dried to give 4.66 g of yellowish crystals. The crystals were recrystallized from acetonitrile. The obtained crystals had a melting point of 198°~201° C and were identified by the elemental analyses and IR spectrum as dichloro bis(4,6-dimethyl-2-pyridylthio)tin(IV).

Found: C, 36.06%; H, 3.40%; N, 6.19%; S, 13.47%; Cl, 15.04%. Calcd. for $C_{14}H_{16}N_2S_2SnCl_2$: C, 36.08%; H, 3.46%; N, 6.01%; S, 13.76%; Cl, 15.22%.

Benzene was recovered by concentration of the benzene solution obtained by filtration leaving 4.66 g of the above yellowish crystals, and the obtained residue was washed with 40 ml of carbon tetrachloride and further with 50 ml of acetonitrile to give 2.81 g of yellowish crystals. The obtained crystals were identified by their melting point and IR spectrum as dichloro bis(4,6-dimethyl-2-pyridylthio)tin(IV).

REFERENTIAL EXAMPLE 9

Synthesis of 4,6-dimethyl-2-pyridinethiol

To 250 ml of a 48 % aqueous hydrobromic acid was added 48.21 g of 3-cyano-4,6-dimethyl-2-pyridinethiol and the mixture was refluxed by heating for 4 hours. During the reflux, the mixture remained as a homogeneous solution. After termination of heating, however, lowering of the temperature caused to precipitate crystals. After cooling to room temperature, the mixture was filtered leaving yellowish crystals. The obtained crystals were recrystallized from 1700 ml of ethanol to give 9.31 g of fine pale-yellowish prisms. In determination of a melting point, the prisms decomposed at 253°~254° C. The prisms were identified by the elemental analyses and IR spectrum (an absorption appeared at 1670 cm$^{-1}$, which is due to carboxylic acid) as 3-carboxy-4,6-dimethyl-2-pyridinethiol.

Found: C, 52.40%; H, 4.99%; N, 7.57%; S, 17.70%. Calcd. for $C_8H_{9NO2}S$: C, 52.44%; H, 4.95%; N, 7.64%; S, 17.50%.

Further, the above aqueous hydrobromic acid obtained by the filtration leaving the above yellowish crystals was diluted with 1500 ml of water and allowed to stand overnight at room temperature to precipitate crystals. The mixture was filtered and the obtained crystals were dried to give 11.64 g of yellowish crystals.

The crystals were recrystallized from 800 ml of acetonitrile and dried to give 7.50 g of yellowish prisms. The obtained prisms had a melting point of 239°~241° C and were identified by the elemental analyses and IR spectrum as 4,6-dimethyl-2-pyridinethiol.

Found: C, 60.42%; H, 6.52%; N, 10.18%; S, 22.74%. Calcd. for $C_7H_9NS$: C, 60.39%; H, 6.52%; N, 10.06%; S, 23.03%.

In addition, said compound can be synthesized by decarboxylation of 3-carboxy-4,6-dimethyl-2-pyridinethiol.

REFERENTIAL EXAMPLE 10

Synthesis of bis(4,6-dimethyl-2-pyridyl) disulfide

An ethanolic solution containing sodium ethoxide was prepared by dissolving 1.11 g of metallic sodium in 60 ml of ethanol. To this solution was added 6.74 g of 4,6-dimethyl-2-pyridinethiol which was prepared in Referential example 9. The mixture was stirred at room temperature to yield a homogeneous solution. To the resulting solution was added dropwise with stirring at room temperature a solution of 6.14 g of iodine in 55 ml of ethanol. After completion of the addition, the reaction mixture was further stirred at room temperature for 1 hour and then concentrated under reduced pressure to recover ethanol. To the residue was added 60 ml of water and the mixture was stirred and filtered leaving insoluble materials. The collected materials were air-dried and dissolved in 55 ml of methanol. By gradual addition of 110 ml of water, the solution gave a precipitate, which was collected by filtration and dried to yield 6.03 g of colorless crystals. The obtained crystals had a melting point of 84.5°~85.0° C and were identified by the elemental analyses and IR spectrum as bis(4,6-dimethyl-2-pyridyl) disulfide.

Found: C, 60.83%; H, 5.93%; N, 10.19%; S, 23.04%. Calcd. for $C_{14}H_{16}N_2S_2$: C, 60.83%; H, 5.83%; N, 10.13%; S, 23.20%.

EXAMPLE 7

Synthesis of dichloro bis(4-methyl-6-phenyl-2-pyridylthio)tin(IV)

To a suspension of 50 ml of benzene containing 4.0 g of bis(4-methyl-6-phenyl-2-pyridyl) disulfide (the synethic method is referred to Referential examples 11 and 12) was added dropwise with stirring at room temperature a solution of 2.26 g of ε-caprolactam and 1.88 g of stannous chloride in 30 ml of benzene. The reaction mixture became a yellow homogeneous solution when an about half of the solution was added. A slightly exothermic reaction occurred and, when the addition was completed, a temperature of the reaction mixture rose by 3° C. After stirring for about 20 minutes from completion of the addition, there began to precipitate yellow crystals. After additional stirring overnight, the reaction mixture was filtered. The collected crystals were dried to give 4.18 g of yellow crystals, which were further recrystallized from acetonitrile. The obtained crystals had a melting point of 210° C and were identified by the elemental analyses and IR spectrum as dichloro bis(4-methyl-6-phenyl-2-pyridylthio)-tin(IV).

Found: C, 48.76%; H, 3.36%; N, 4.97%; S, 10.66%; Cl, 11.77%. Calcd. for $C_{24}H_{20}N_2S_2SnCl_2$: C, 48.85%; H, 3.42%; N, 4.75%; S, 10.87%; Cl, 12.07%.

The benzene solution obtained by filtration leaving 4.18 g of the above yellow crystals was concentrated to recover benzene. The residue was washed with 40 ml of carbon tetrachloride and further with 40 ml of acetonitrile to yield 0.95 g of yellow crystals. The obtained crystals were identified by the melting point and IR spectrum as dichloro bis(4-methyl-6-phenyl-2-pyridylthio)tin(IV).

REFERENTIAL EXAMPLE 11

Synthesis of 4-methyl-6-phenyl-2-pyridinethiol

To 300 ml of a 48 % aqueous hydrobromic acid was added 24.0 g of 3-cyano-4-methyl-6-phenyl-2-pyridinethiol and the mixture was refluxed by heating for 4 hours. During reflux, the mixture was a homogeneous solution, but there began to precipitate crystals with spontaneous cooling. The reaction mixture was poured into 1 l of ice-water. After stirring, the mixture was filtered leaving a mixed residue of crystals with oil. Said residue was washed with 60 ml of ethanol and dried to yield 8.0 g of yellowish crystals. The crystals were recrystallized from 200 ml of a mixture of water and ethanol (3:1 in volume ratio) to give 5.13 g of fine yellowish prisms. The obtained prisms had a melting point of 168°~171° C and were identified by the elemental analyses and IR spectrum as 4-methyl-6-phenyl-2-pyridinethiol.

Found: C, 71.40%; H, 5.26%; N, 6.80%; S, 15.31%. Calcd. for $C_{12}H_{11}NS$: C, 71.61%; H, 5.51%; N, 6.96%; S, 15.93%.

REFERENTIAL EXAMPLE 12

Synthesis of bis(4-methyl-6-phenyl-2-pyridyl) disulfide

An ethanolic solution containing sodium ethoxide was prepared by dissolving 0.57 g of metallic sodium in 40 ml of ethanol. To this solution was added 5.00 g of 4-methyl-6-phenyl-2-pyridinethiol and the mixture was stirred at room temperature. To the obtained yellow-orange suspension was added dropwise with stirring at room temperature a solution of 3.16 g of iodine in 40 ml of ethanol. With addition, the suspended yellow-orange material was dissolved and simultaneously colorless crystals newly began to crystallize out. After completion of the addition, stirring was continued at room temperature for 3 hours and the reaction mixture was filtered. The collected crystals were dried to yield 4.0 g of colorless powdery crystals. The obtained crystals had a melting point of 154° C and were identified by the elemental analyses and IR spectrum as bis(4-methyl-6-phenyl-2-pyridyl) disulfide.

Found: C, 71.45%; H, 4.78%; N, 6.95%; S, 15.48%. Calcd. for $C_{24}H_{20}N_2S_2$: C, 71.97%; H, 5.03%; N, 6.99%; S, 16.01%.

EXAMPLE 8

Synthesis of dichloro bis(2-pyridylthio)tin(IV)

To a solution of 2.84 g of stannous chloride and 10 ml of tetrahydrofuran in 40 ml of ethylene dichloride was added dropwise with stirring at room temperature a solution of 3.31 g of 2,2'-dipyridyl disulfide in 60 ml of ethylene dichloride. With addition, there gradually precipitated yellowish crystals. After completion of the addition, stirring was continued at room temperature for 3 hours and the reaction mixture was filtered. The collected crystals were dried to yield 5.36 g of almost colorless crystals with slight yellowness. The obtained crystals were identified by their melting points and IR spectrum as dichloro bis(2-pyridylthio)tin(IV).

EXAMPLE 9

Synthesis of dichloro bis(2-pyridylthio)tin(IV)

In 20 ml of dimethylformamide was dissolved 2.84 g of stannous chloride. A slightly exothermic reaction occurred and a temperature of the solution rose by 6° C. To this solution was added dropwise with stirring at room temperature a solution of 3.31 g of 2,2'-dipyridyl disulfide in 20 ml of dimethylformamide. When the addition was completed, the mixture was a yellowish homogeneous solution. However, after further stirring for about 6 minutes, there began to precipitate crystals. Additional stirring was continued for 3 hours and a half, and the reaction mixture was filtered. The collected crystals were dried to yield 4.68 g of almost colorless crystals with slight yellowness. The obtained crystals were identified by their melting point and IR spectrum as dichloro bis(2-pyridylthio)tin(IV). In addition, the dimethylformamide solution obtained by filtration leaving the above crystals was concentrated. The obtained residue was washed with ethylene dichloride to yield another 1.32 g of crystals. The crystals were also identified by their melting points and IR spectrum as dichloro bis(2-pyridylthio)tin(IV).

EXAMPLE 10

Synthesis of dichloro bis(2-pyridylthio)tin(IV)

Same procedure as Example 8 except using 10 ml of diethylene glycol dimethyl ether instead of 10 ml of tetrahydrofuran yielded 5.66 g of dichloro bis(2-pyridylthio)tin(IV) as almost colorless crystals with slight yellowness.

EXAMPLE 11

Synthesis of dichloro bis(2-pyridylthio)tin(IV)

Same procedure as Example 8 except using 8 g of dimethyl sulfoxide instead of 10 ml of tetrahydrofuran yielded 5.23 g of dichloro bis(2-pyridylthio)tin(IV) as almost colorless crystals with slight yellowness.

EXAMPLE 12

Synthesis of dichloro bis(2-pyridylthio)tin(IV)

To a stirred suspension of 18.96 g of stannous chloride in 80 ml of ethylene dichloride was added dropwise at room temperature a solution of 22.03 g of 2,2'-dipyridyl disulfide in 80 ml of ethylene dichloride. After completion of the addition, stirring was continued for 5 hours and the reaction mixture was filtered. The collected substance was washed with three 30 ml portions of ethylene dichloride and dried to give 39.02 g of almost colorless crystals with slight yellowness. The obtained crystals were identified by their melting points and IR spectrum as dichloro bis(2-pyridylthio)tin(IV).

EXAMPLE 13

Synthesis of dichloro bis(2-pyridylthio)tin(IV)

In an atmosphere of dry nitrogen, 5.51 g of 2,2'-dipyridyl disulfide and 4.74 g of stannous chloride were mixed and ground to a powder. The mixture was heated to 90° C on an oil bath. Upon heating, the mixture became to a gruel and then solidified to a caramel. After heating for 1 hour, the solid was allowed to stand and ground to a powder in an atmosphere of dry nitrogen. The obtained powdery solid was identified by its melting point and IR spectrum as dichloro bis(2-pyridylthio)tin(IV).

In order to remove trace amounts of unreacted substance, said powdery solid was treated as follows. Namely, the solid was added to 60 ml of ice-water, and the mixture was stirred for 10 minutes and filtered. The collected substance was washed with two 10 ml portions of cooled water to remove completely water-soluble stannous chloride. The residue was dried and suspended in 50 ml of benzene. After stirring for 10 minutes, the suspension was filtered. The collected substance was washed with 30 ml of benzene to remove benzene-soluble 2,2'-dipyridyl disulfide and dried to give 10.00 g of an almost colorless powder with slight yellowness. The obtained powder was identified by its melting point and IR spectrum as dichloro bis(2-pyridylthio)tin(IV).

EXAMPLE 14

Synthesis of diiodo bis(2-pyridylthio)tin(IV)

To a stirred suspension of 7.95 g of stannous iodide (purity: 85 %) in 40 ml of ethylene dichloride was added dropwise at room temperature a solution of 4.00 g of 2,2'-dipyridyl disulfide in 60 ml of ethylene dichloride. With addition, suspended red-orange stannous iodide gradually dissolved and yellow-orange crystals newly began to precipitate. A slightly exothermic reaction occurred and a temperature of the reaction mixture rose by 3° C. After completion of the addition, the mixture was stirred at room temperature for 3 hours and filtered. The collected crystals were dried to give 9.05 g of yellow-orange crystals. Crystals recrystallized from ethylene dichloride had a melting point of 271°~273° C and were identified by the elemental analyses and IR spectrum as diiodo bis(2-pyridylthio)tin(IV).

Found: C, 20.18%; H, 1.24%; N, 4.95%; S, 10.63%; I, 43.09%. Calcd. for $C_{10}H_8N_2S_2SnI_2$: C, 20.26%; H, 1.36%; N, 4.73%; S, 10.82%; I, 42.81%.

EXAMPLE 15

Synthesis of dichloro bis(5-nitro-2-pyridylthio)tin(IV)

A solution of 0.85 g of ε-caprolactam and 0.71 g of stannous chloride in 30 ml of benzene was added dropwise with stirring at room temperature to 60 ml of benzene solution containing 1.17 g of bis(5-nitro-2-pyridyl) disulfide. The resultant mixture was a yellow-orange homogeneous solution. The solution was stirred at room temperature for 30 minutes and concentrated under reduced pressure to remove benzene. To the obtained oily residue was added 100 ml of carbon tetrachloride and the mixture was stirred. Decantation was conducted to remove carbon tetrachloride. The obtained caramel-like-substance insoluble in carbon tetrachloride was, after addition of 60 ml of isopropanol, stirred to crystallize gradually. The crystals were collected by filtration and dried to yield 1.26 g of yellowish crystals, having a melting point of 188°~197° C. The crystals were recrystallized from acetonitrile and identified by the elemental analyses and IR spectrum as dichloro bis(5-nitro-2-pyridylthio)tin(IV). mp 260°~262° C (decomp.)

Found: C, 24.33%; H, 1.30%; N, 11.38%; S, 13.07%; Cl, 14.14%. Calcd. for $C_{10}H_6N_4O_4S_2SnCl_2$: C, 24.03%; H, 1.20%; N, 11.21%; S, 12.83%; Cl, 14.18%.

EXAMPLE 16

Synthesis of dichloro bis(3-ethoxycarbonyl-6-methyl-2-pyridylthio)tin(IV)

A solution of 2.20 g of ε-caprolactam and 1.85 g of stannous chloride in 40 ml of benzene was added dropwise to a suspension of 50 ml of benzene containing 3.82 g of bis(3-ethoxycarbonyl-6-methyl-2-pyridyl) disulfide (the synthetic method is referred to Referential examples 13 and 14). With addition, the suspended material gradually dissolved and, when the addition was completed, there was obtained a homogeneous solution. After stirring for 2 hours and a half at room temperature, benzene was removed from the reaction mixture. The obtained oily residue was, after addition of 100 ml of carbon tetrachloride, stirred to crystallize gradually. The mixture became to a suspension of colorless crystals after 30 minutes. After filtration, the collected crystals were dried to yield 4.76 g of colorless crystals. The crystals were recrystallized from 80 ml of ethanol to give 3.37 g of colorless needles. The obtained needles had a melting point of 165.5°~166° C and were identified by the elemental analyses and IR spectrum as dichloro bis(3-ethoxycarbonyl-6-methyl-2-pyridylthio)tin(IV).

Found: C, 37.20%; H, 3.37%; N, 4.96%; S, 11.09%; Cl, 12.37%. Calcd. for $C_{18}H_{20}N_2O_4S_2SnCl_2$: C, 37.14%; H, 3.46%; N, 4.81%; S, 11.02%; Cl, 12.18%.

REFERENTIAL EXAMPLE 13

Synthesis of 3-ethoxybarbonyl-6-methyl-2-pyridinethiol

To 200 ml of ethanol was added 14.44 g of 3-carboxy-6-methyl-2-pyridinethiol, and the mixture was refluxed by heating for 5 hours during which dry hydrogen chloride gas was introduced into the mixture through a capillary. During reflux, the reaction mixture is a homogeneous solution. But, while stirring was continued after termination of reflux, there began to precipitate crystals. The reaction mixture was allowed to stand overnight and filtered leaving 9.60 g of crystals. The crystals were dissolved in 80 ml of water and neutralized with a 10 % aqueous sodium hydrogen carbonate. The precipitated crystals were collected by filtration and recrystallized from 1500 ml of isopropyl ether to give 5.41 g of pale-yellow prisms. The prisms had a melting point of 129°~131° C and were identified by the elemental analyses and IR spectrum as 3-ethoxycarbonyl-6-methyl-2-pyridinethiol.

Found: C, 54.69%; H, 5.40%; N, 7.11%; S, 16.23%. Calcd. for $C_9H_{11}NO_2S$: C, 54,80%; H, 5.62%; N, 7.10%; S, 16.22%.

REFERENTIAL EXAMPLE 14

Synthesis of bis(3-ethoxycarbonyl-6-methyl-2-pyridyl) disulfide

An ethanolic solution containing sodium ethoxide was prepared by dissolving 0.63 g of metallic sodium in 80 ml of ethanol. To this solution was added 5.35 g of 3-ethoxycarbonyl-6-methyl-2-pyridinethiol, and the mixture was stirred to give a yellowish homogeneous solution. To the solution was added dropwise with stirring at room temperature 40 ml of ethanol containing 3.45 g of iodine. With addition, there began to precipitate colorless crystals. After completion of the addition, stirring was continued for 30 minutes at room temperature, and the reaction mixture was filtered. The collected crystals were dried to yield 5.1 g of colorless crystals. The crystals were recrystallized from 35 ml of carbon tetrachloride to give 3.95 g of colorless prisms. The obtained crystals had a melting point of 138°~140° C and were identified by the elemental analyses and IR spectrum as bis(3-ethoxycarbonyl-6-methyl-2-pyridyl) disulfide.

Found: C, 54.88%; H, 5.06%; N, 7.31%; S, 16.14%. Calcd. for $C_{18}H_{20}N_2O_4S_2$: C, 55.08%; H, 5.14%; N, 7.14%; S, 16.34%.

EXAMPLE 17

Synthesis of dichloro bis(3-cyano-6-methyl-2-pyridylthio)tin(IV)

A solution of 3.79 g of ε-caprolactam and 3.18 g of stannous chloride in 90 ml of benzene was added dropwise with stirring at room temperature to a suspension comprising 70 ml of benzene and 5.0 g of bis(3-cyano-6-methyl-2-pyridyl) disulfide (the synthetic method is referred to Referential example 15). With addition, a slightly exothermic reaction occurred, and a temperature of the reaction mixture rose by 2° C, and crystals newly precipitated. After completion of the addition, the mixture was stirred at room temperature for 1 hour and refluxed by heating for 1 hour. The reaction mixture was left to reach room temperature and filtered. The collected residue was dried to yield 6.36 g of yellowish crystals. The crystals were recrystallized from acetonitrile to give yellowish prisms. The obtained prisms had a melting point of 262°~265° C (decomp.) and were identified by the elemental analyses and IR spectrum as dichloro bis(3-cyano-6-methyl-2-pyridylthio)tin(IV).

Found: C, 34.79%; H, 2.13%; N, 11.95%; S, 13.38%; Cl, 14.30%. Calcd. for $C_{14}H_{10}N_4S_2SnCl_2$: C, 34.47%; H, 2.07%; N, 11.48%; S, 13,14%; Cl, 14.53%.

REFERENTIAL EXAMPLE 15

Synthesis of bis(3-cyano-6-methyl-2-pyridyl) disulfide

An ethanolic solution containing sodium ethoxide was prepared by dissolving 1.91 g of metallic sodium in 80 ml of ethanol. To this solution was added 12.47 g of 3-cyano-6-methyl-2-pyridinethiol, and the mixture was stirred at room temperature for a few minutes to give a homogeneous solution. To the solution was added dropwise with stirring at room temperature 100 ml of an ethanolic solution containing 10.54 g of iodine. In a few minutes after completion of the addition, there began to precipitate crystals. The mixture was stirred for 1 hour and a half, and then filtered. The collected crystals were dried to yield 9.93 g of pale yellow-brown crystals. The crystals were recrystallized from 800 ml of isopropanol to give 8.47 g of pale yellow-brown prisms. The obtained prisms had a melting point of 172°~173° C and were identified by the elemental analyses and IR spectrum as bis(3-cyano-6-methyl-2-pyridyl) disulfide.

Found: C, 56.47%; H, 3.43%; N, 18.29%; S, 21.99%. Calcd. for $C_{14}H_{10}N_4S_2$: C, 56.36%; H, 3.38%; N, 18.78%; S, 21.49%.

The following referential examples show an excellent stabilizing effect of the pyridinethiol-tin compounds obtained according to this invention against deterioration caused by contact of a polyolefin with a heavy metal. The term "part" means weight part and Melt flow Index (M. I.) was determined in accordance with ASTMD 1238. In addition, the notations shown in Tables means the following compounds.

A; Dichloro bis(2-pyridylthio)tin(IV)
B; Dibromo bis(2-pyridylthio)tin(IV)
C; Dichloro bis(3-cyano-4,6-dimethyl-2-pyridylthio)tin(IV)
D; Dichloro bis(3-cyano-4-methyl-6-phenyl-2-pyridylthio)tin(IV)
E; Dichloro bis(N-oxido-2-pyridylthio)tin(IV)
F; Dichloro bis(4,6-dimethyl-2-pyridylthio)tin(IV)
G; Dichloro bis(4-methyl-6-phenyl-2-pyridylthio)tin(IV)
H; Dichloro bis(5-nitro-2-pyridylthio)tin(IV)
I; Dichloro bis(3-ethoxycarbonyl-6-methyl-2-pyridylthio)tin(IV)
J; Dichloro bis(3-cyano-6-methyl-2-pyridylthio)tin(IV)
K; Diiodo bis(2-pyridylthio)tin(IV)
a; MARK-CDA-1 (trade name, available from Adeka-Argus chemical industry Co., Ltd.)

REFERENTIAL EXAMPLES 16 – 37

1. Preparation of test piece

Into a Brabenter plastograph (available from Brabender Corporation, West Germany) adjusted to 60 r.p.m. of rotation speed and a temperature of 140° C were charged 100 parts of ethylene homopolymer (M.I. = 0.2) with no additives prepared by a high pressure process. Two minutes later, 0.10 part of an antioxidant, tetrakis [3-(3,5-di-tert-butyl-4-hydroxyphenyl)propionyloxymethyl]methane, and a fixed amount of the pyridinethiol-tin compound was added thereto. Further, another 2 minutes later, 0.10 part of copper stearate was added to the mixture, which was subsequently kneaded for 8 minutes. The mixture was then heated on a plate of 190° C for 1 minute by means of the spacer and was pressed at a pressure of 300 kg/cm² for 1 minute to form a film having a thickness of 0.25 mm. A round film of 4 mm in its diameter was prepared by punching of the obtained film, and employed as a test piece.

2. Determination of anti-deterioration effect

The time required for appearance of a peak showing generation of heat caused by oxidation was determined by means of a Standard-Type Rapidly Fluctuating Differential Calorimeter (available from Rigaku Denki Kogyo Ltd., Japan). The calorimeter received a test piece in one sample dish and the other dish remained empty. After the atmosphere of the calorimeter was replaced with oxygen, the environmental temperature was elevated to 195° C in an instant (about 5 – 10 seconds) by means of an inside heating system, then elevated to 200° C in about 30 seconds and kept at this temperature, during which process oxygen was made to flow therethrough at a rate of 180 ml/min. The induction period herein means the period from the time when the temperature rose to 200° C to the time when there appeared a peak showing generation of heat caused by oxidation of a test piece. The period determined as above was adopted to estimate an anti-deterioration effect.

The results obtained according to the above-mentioned process are shown in Table 1.

Table 1

| Ref. example | Kind and amount (part) of compound | | Induction period (min.) |
|---|---|---|---|
| 16 | A | 0.05 | 17 |

Table 1-continued

| Ref. example | Kind and amount (part) of compound | | Induction period (min.) |
|---|---|---|---|
| 17 | '' | 0.10 | 35 |
| 18 | '' | 0.15 | 65 |
| 19 | B | 0.15 | 70 |
| 20 | C | 0.15 | 50 |
| 21 | D | 0.15 | 51 |
| 22 | E | 0.05 | 21 |
| 23 | '' | 0.10 | 54 |
| 24 | '' | 0.15 | 114 |
| 25 | '' | 0.50 | 186 |
| 26 | F | 0.05 | 35 |
| 27 | '' | 0.10 | 74 |
| 28 | '' | 0.15 | 140 |
| 29 | '' | 0.50 | 210 |
| 30 | G | 0.05 | 38 |
| 31 | '' | 0.10 | 78 |
| 32 | '' | 0.15 | 140 |
| 33 | '' | 0.50 | 215 |
| 34 | H | 0.15 | 76 |
| 35 | I | 0.15 | 72 |
| 36 | J | 0.15 | 53 |
| 37 | K | 0.15 | 80 |

REFERENTIAL EXAMPLES 38 – 58

1. Preparation of test piece

Into a Brabender plastograph referred to the above Referential example 16 and adjusted to 50 r.p.m. of rotation speed and a temperature of 200° C were charged 100 parts of isotactic polypropylene (M.I. = 1) with no additives. Two minutes later, 0.60 part of tetrakis[3-(3,5-di-tert-butyl-4-hydroxyphenyl)propionyloxymethyl]methane, and the kind and an amount of a compound shown in Table 2 were added thereto, and the mixture was subsequently kneaded for 8 minutes. The mixture was then heated on a plate of 190° C for 1 minute by means of the spacer and was pressed at a pressure of 300 kg/cm² for 1 minute to form a film having a thickness of 0.25 mm. A round film of 6 mm in its diameter was prepared by punching of the obtained film, and employed as a test piece.

2. Determination of anti-deterioration effect

The time required for appearance of a peak showing generation of heat caused by oxidation was determined by means of a Differential Calorimeter (available from Parkin-Elmer Corporation). The calorimeter received a test piece in one sample dish on which a copper plate of 0.10 mm in thickness and 6 mm in diameter was put and the other dish with the same copper plate remained empty. After the atmosphere of the calorimeter was replaced with nitrogen, the environmental temperature was elevated to 200° C at a rate of 8° C/min. in a stream of nitrogen at a rate of 400 ml/min. When the temperature reached 200° C, the nitrogen stream was replaced with oxygen at the same rate. The induction period herein means the period from the time of this replacement with oxygen to the time when there appeared a peak showing generation of heat caused by oxidation of a test piece. The period determined as above was adopted to estimate an anti-deterioration effect.

The results obtained according to the above-mentioned process are shown in Table 2.

Table 2

| Ref. example | Kind of compound | Amount (part) | Induction period (min.) |
|---|---|---|---|
| 38 | A | 0.10 | 65 |
| 39 | '' | 0.15 | 79 |
| 40 | '' | 0.30 | 121 |
| 41 | B | 0.30 | 111 |
| 42 | C | 0.30 | 105 |

Table 2-continued

| Ref. example | Kind of compound | Amount (part) | Induction period (min.) |
|---|---|---|---|
| 43 | D | 0.30 | 108 |
| 44 | E | 0.10 | 70 |
| 45 | " | 0.15 | 82 |
| 46 | " | 0.30 | 137 |
| 47 | F | 0.10 | 75 |
| 48 | " | 0.15 | 87 |
| 49 | " | 0.30 | 140 |
| 50 | G | 0.10 | 69 |
| 51 | " | 0.15 | 83 |
| 52 | " | 0.30 | 138 |
| 53 | H | 0.10 | 78 |
| 54 | " | 0.15 | 85 |
| 55 | " | 0.30 | 130 |
| 56 | I | 0.30 | 126 |
| 57 | J | 0.30 | 109 |
| 58 | K | 0.30 | 131 |

REFERENTIAL COMPARATIVE EXAMPLE 1

Same procedure as Referential example 16 except using 0.15 part of MARK-CDA-1 (a) instead of dichloro bis(2-pyridylthio)tin(IV) was conducted to give 34 minutes of the induction period.

REFERENTIAL COMPARATIVE EXAMPLE 2

Same procedure as Referential example 38 except using 0.30 part of MARK-CDA-1 (a) instead of dichloro bis(2-pyridylthio)tin(IV) was conducted to give 44 minutes of the induction period.

What is claimed is:

1. A pyridinethio-tin compound having the formula RS-SnX$_2$-SR wherein R represents a group having the formula

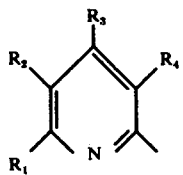

wherein each of R$_1$-R$_4$ represents a group selected from the group consisting of a hydrogen atom, a nitro group, a cyano group, an alkoxycarbonyl group having from 2 to 11 carbon atoms, a phenyl group, and a linear alkyl group having from 1 to 4 carbon atoms, not less than two groups among R$_1$-R$_4$ being selected from the group consisting of a hydrogen atom and said linear alkyl group, and X represents an atom which is selected from the group consisting of fluorine, chlorine, bromine and iodine.

2. The pyridinethiol-tin compound of claim 1, wherein each of R$_1$-R$_4$ is hydrogen.
3. Dichloro bis(2-pyridylthio)tin(IV) of claim 1.
4. Dibromo bis(2-pyridylthio)tin(IV) of claim 1.
5. Dichloro bis(3-cyano-4,6-dimethyl-2-pyridylthio)tin(IV) of claim 1.
6. Dichloro bis(3-cyano-4-methyl-6-phenyl-2-pyridylthio)tin(IV) of claim 1.
7. Dichloro bis(4,6-dimethyl-2-pyridylthio)tin(IV) of claim 1.
8. Dichloro bis(4-methyl-6-phenyl-2-pyridylthio)tin(IV) of claim 1.
9. Dichloro bis(5-nitro-2-pyridylthio)tin(IV) of claim 1.
10. Diodo bis(2-pyridlythio)tin(IV) of claim 1.
11. Dichloro bis(3-ethoxycarbonyl-6-methyl-2-pyridylthio)tin(IV) of claim 1.
12. Dichloro bis(3-cyano-6-methyl-2-pyridylthio)tin(IV) of claim 1.
13. The pyridinethiol-tin compound of claim 1, wherein one of R$_1$-R$_4$ is a nitro group.
14. The pyridinethiol-tin compound of claim 1, wherein one of R$_1$-R$_4$ is a cyano group.
15. The pyridinethiol-tin compound of claim 1, wherein one of R$_1$-R$_4$ is an alkoxycarbonyl group having from 2 to 11 carbon atoms.
16. The pyridinethiol-tin compound of claim 1, wherein one of R$_1$-R$_4$ is an ethoxycarbonyl group.
17. The pyridinethiol-tin compound of claim 1, wherein one of R$_1$-R$_4$ is a methoxycarbonyl group.
18. The pyridinethiol-tin compound of claim 1, wherein one of R$_1$-R$_4$ is a phenyl group.
19. The pyridinethiol-tin compound of claim 1, wherein each of R$_1$-R$_4$ is a linear alkyl group having from 1 to 4 carbon atoms.

* * * * *

UNITED STATES PATENT AND TRADEMARK OFFICE
CERTIFICATE OF CORRECTION

Page 1 of 3

PATENT NO. : 4,009,168
DATED : February 22, 1977
INVENTOR(S) : MITSUO MASAKI et al It is certified that error appears in the above-identified patent and that said Letters Patent are hereby corrected as shown below:

Column 1, lines 35-36: after "having", insert ---carbon---.

Column 3, line 6: rewrite "N-oxido-- 5" as
---N-oxido-5---.

Column 3, line 8: rewrite "N-oxido-- 3" as
---N-oxido-3---.

Column 3, line 14: rewrite "IV-oxido" as ---N-oxido---.

Column 5, line 5: rewrite "N-oxido-- 4" as
---N-oxido-4---.

Column 5, line 14: rewrite "pyridyltho" as
---pyridylthio---.

Column 9, line 27: replace "Cl, 29.335%" with
--- Cl, 29.35% ---.

Column 10, line 27: replace "159°" with ---259°---.

Column 12, line 61: replace "$C_8H_9NO_2S$" with ---$C_8H_9NO_2S$---.

Column 13, lines 45-46: replace "synetic" with
---synthetic---.

Column 13, line 62: rewrite "pyridylthio)-tin" as
---pyridylthio)tin---.

UNITED STATES PATENT AND TRADEMARK OFFICE
CERTIFICATE OF CORRECTION

PATENT NO. : 4,009,168
DATED : February 22, 1977
INVENTOR(S) : MITSUO MASAKI et al It is certified that error appears in the above-identified patent and that said Letters Patent are hereby corrected as shown below:

Column 3, line 34: after "and", insert ---a---.

Column 5, line 56: replace "has" with ---have---.

Column 6, lines 10-11: rewrite "condition" as ---conditions---.

Column 6, line 63: rewrite "make" as ---makes---.

Column 6, line 67: after "which", insert ---a---.

Column 7, line 5: after "containing", insert ---a---.

Column 7, line 7: replace "letting" with ---setting---.

Column 19, line 1: rewrite "ASTMD 1238" as ---ASTM D1238---.

Column 19, lines 36-38: delete "by means of...1 minute" and replace with ---and was pressed at a pressure of 300 kg/cm$^2$ for 1 minute by means of the spacer---.

Column 20, lines 35-36: delete "by means of...1 minute" and replace with ---and was pressed at a pressure of 300 kg/cm$^2$ for 1 minute by means of the spacer---.

Column 20, line 44: rewrite "Parkin" as ---Perkin---.

UNITED STATES PATENT OFFICE
CERTIFICATE OF CORRECTION

Patent No. 4,009,168      Dated February 22, 1977

Inventor(s) Mitsuo Masaki et al.

It is certified that error appears in the above-identified patent and that said Letters Patent are hereby corrected as shown below:

Column 16, line 57: rewrite "like-substance" as ---like substance---.

Column 18, line 68: rewrite "flow" as ---Flow---.

Column 19, line 2: rewrite "means" as ---mean---.

Column 19, line 24: rewrite "Brabenter" as ---Brabender---.

Column 21, line 34: replace "pyridinethio" with ---pyridinethiol---.

Column 22, line 25: replace "Diodo" with ---Diiodo---.

Signed and Sealed this

Twenty-eighth Day of February 1978

[SEAL]

Attest:

RUTH C. MASON
Attesting Officer

LUTRELLE F. PARKER
Acting Commissioner of Patents and Trademarks